(12) United States Patent
McCabe et al.

(10) Patent No.: US 10,792,196 B2
(45) Date of Patent: Oct. 6, 2020

(54) APPARATUS AND METHOD FOR HIGH SPEED CROSS FOLDING

(71) Applicant: CURT G. JOA, INC., Sheboygan Falls, WI (US)

(72) Inventors: John A. McCabe, Sheboygan Falls, WI (US); Gottfried Jason Hohm, Sheboygan Falls, WI (US); Anthony A. Nelson, New Holstein, WI (US); Zachary J. Giffey, Sheboygan Falls, WI (US)

(73) Assignee: Curt G. Joa, Inc., Sheboygan Falls, WI (US)

( * ) Notice: Subject to any disclaimer, the term of this patent is extended or adjusted under 35 U.S.C. 154(b) by 305 days.

(21) Appl. No.: 14/162,399

(22) Filed: Jan. 23, 2014

(65) Prior Publication Data

US 2015/0202092 A1 Jul. 23, 2015

(51) Int. Cl.
*A61F 13/15* (2006.01)
*B65H 45/12* (2006.01)

(52) U.S. Cl.
CPC ....... *A61F 13/15747* (2013.01); *B65H 45/12* (2013.01); *B65H 2404/2321* (2013.01); *B65H 2404/62* (2013.01); *B65H 2801/57* (2013.01)

(58) Field of Classification Search
CPC ......... B31F 1/30; B65H 45/16; B65H 45/147; B65H 45/04; B65H 45/161; B65H 2404/232; B65H 2404/2321; B65H 2404/311; B65H 29/38; A61F 13/15747; B32B 2555/02; B31B 70/261; B31B 70/52

USPC ....... 493/416, 418, 422, 423, 424, 425, 427, 493/434, 435, 438, 442, 450; 198/817, 198/604
See application file for complete search history.

(56) References Cited

U.S. PATENT DOCUMENTS

| | | | | |
|---|---|---|---|---|
| 3,572,689 A | * | 3/1971 | Murphy ................. | B65H 45/12 493/422 |
| 4,157,058 A | * | 6/1979 | Vogel ....................... | B31B 1/06 493/124 |
| 4,285,621 A | * | 8/1981 | Spencer ................. | B65H 29/38 414/790 |

(Continued)

FOREIGN PATENT DOCUMENTS

WO  WO2012/123813 A1  9/2012

OTHER PUBLICATIONS

Supplementary European Search Report dated Sep. 21, 2017 regarding EP Appl. No. 14880017, 5 pages.

(Continued)

*Primary Examiner* — Dariush Seif
(74) *Attorney, Agent, or Firm* — Ziolkowski Patent Solutions Group, SC

(57) ABSTRACT

Apparatus and methods are provided for folding discrete items such as diapers at high speeds. Discrete items are conveyed in a machine direction toward a pair of vacuum drums rotating in the machine direction and first carrying a top side of a leading edge of the discrete item away from the conveyor, and then carrying a bottom side of the leading edge with a second rotational vacuum drum back towards the conveyor. The diaper fold is created at a contact point with a folding finger which travels rotationally and straight in a fixed orientation about a pair of belts, into and out of contact with the diaper.

17 Claims, 13 Drawing Sheets

(56) References Cited

U.S. PATENT DOCUMENTS

| | | | |
|---|---|---|---|
| 4,360,194 A * | 11/1982 | Bradley | B65H 35/04 |
| | | | 270/42 |
| 4,508,528 A * | 4/1985 | Hirsch | B65H 45/18 |
| | | | 270/45 |
| 4,549,876 A * | 10/1985 | Baker | B31B 1/00 |
| | | | 493/169 |
| 4,616,815 A | 10/1986 | Vijuk | |
| 4,717,375 A * | 1/1988 | Lundmark | A61F 13/15747 |
| | | | 493/357 |
| 4,938,739 A * | 7/1990 | Nilsson | B01D 29/012 |
| | | | 493/422 |
| 5,074,547 A | 12/1991 | Smith et al. | |
| 5,152,734 A | 10/1992 | McAdam, III et al. | |
| 5,788,805 A * | 8/1998 | Herrmann | A61F 13/15577 |
| | | | 156/443 |
| 5,795,433 A | 8/1998 | Niedermeyer | |
| 6,086,522 A * | 7/2000 | Hechler | B65H 45/144 |
| | | | 493/18 |
| 6,514,187 B2 | 2/2003 | Coenen et al. | |
| 7,264,583 B2 * | 9/2007 | Gelli | B65H 31/28 |
| | | | 493/360 |
| 7,384,386 B2 * | 6/2008 | Sosalla | A61F 13/15747 |
| | | | 493/441 |
| 7,399,266 B2 * | 7/2008 | Aiolfi | B65B 63/045 |
| | | | 493/418 |
| 8,257,237 B2 | 9/2012 | Burns, Jr. et al. | |
| 8,439,814 B2 * | 5/2013 | Piantoni | A61F 13/15747 |
| | | | 493/416 |
| 8,485,956 B2 | 7/2013 | Burns, Jr. et al. | |
| 8,617,040 B2 | 12/2013 | Coenen et al. | |
| 8,870,732 B2 * | 10/2014 | Schneider | A61F 13/15747 |
| | | | 493/416 |
| 2004/0063559 A1 * | 4/2004 | Ochsenbauer | B31F 1/0019 |
| | | | 493/427 |
| 2005/0092440 A1 * | 5/2005 | Lindsay | B43M 5/047 |
| | | | 156/442.1 |
| 2006/0276320 A1 | 12/2006 | Aiolfi et al. | |
| 2007/0129230 A1 | 6/2007 | Sosalla | |
| 2008/0026925 A1 * | 1/2008 | Allen | A61F 13/15682 |
| | | | 493/423 |
| 2010/0263987 A1 * | 10/2010 | Meyer | A61F 13/15764 |
| | | | 198/461.1 |
| 2011/0003673 A1 | 1/2011 | Piantoni et al. | |
| 2011/0251040 A1 * | 10/2011 | Yamamoto | A61F 13/15747 |
| | | | 493/418 |
| 2012/0157288 A1 * | 6/2012 | Coenen | B65H 45/16 |
| | | | 493/435 |
| 2012/0302418 A1 | 11/2012 | Burns, Jr. et al. | |
| 2013/0270065 A1 | 10/2013 | Papsdorf et al. | |
| 2014/0171284 A1 | 6/2014 | Coenen et al. | |
| 2016/0194174 A1 * | 7/2016 | Schoulz | B65H 45/16 |
| | | | 493/418 |

OTHER PUBLICATIONS

Extended European Search Report dated Jun. 24, 2019 regarding EP Application No. 18215765.1, 11 pages.

* cited by examiner

US 10,792,196 B2

APPARATUS AND METHOD FOR HIGH SPEED CROSS FOLDING

BACKGROUND OF THE INVENTION

The invention disclosed herein relates to apparatus and methods for folding discrete pieces traveling on a production line. While the description provided relates to diaper manufacturing, the apparatus and method are easily adaptable to other applications.

Generally, diapers comprise an absorbent insert or patch and a chassis, which, when the diaper is worn, supports the insert proximate a wearer's body. Additionally, diapers may include other various patches, such as tape tab patches, reusable fasteners and the like. The raw materials used in forming a representative insert are typically cellulose pulp, tissue paper, poly, nonwoven web, acquisition, and elastic, although application specific materials are sometimes utilized. Usually, most of the insert raw materials are provided in roll form, and unwound and applied in assembly line fashion.

In the creation of a diaper, multiple roll-fed web processes are typically utilized. To create an absorbent insert, the cellulose pulp is unwound from the provided raw material roll and pulverized by a pulp mill. Discrete pulp cores are formed by a core forming assembly and placed on a continuous tissue web. Optionally, super-absorbent powder may be added to the pulp core. The tissue web is wrapped around the pulp core. The wrapped core is debulked by proceeding through a calendar unit, which at least partially compresses the core, thereby increasing its density and structural integrity. After debulking, the tissue-wrapped core is passed through a segregation or knife unit, where individual wrapped cores are cut. The cut cores are conveyed, at the proper pitch, or spacing, to a boundary compression unit.

The diaper is built by sandwiching the formed core between a backsheet and a topsheet, and the combined web receives ears for securing the diaper about the waist of a baby.

Most products require some longitudinal folding. It can be combined with elastic strands to make a cuff. It can be used to overwrap a stiff edge to soften the feel of the product. It can also be used to convert the final product into a smaller form to improve the packaging.

Diapers are typically formed in a machine direction in a generally flat condition. Formed diapers require folding both longitudinally to tuck the ears and associated tape or hook applicators into the diaper, and also cross-folded generally at a crotch region to stack the diapers prior to packaging.

The folded product is then passed downstream to a packaging machine where the diapers are stacked and packaged and shipped for sale.

SUMMARY OF THE INVENTION

Provided are method and apparatus for minimizing waste and improving quality and production in web processing operations.

Importantly, the methods taught in the present application are applicable not only to diapers and the like, but in any web based operation. The folding techniques taught herein can be directed any discrete component of a manufactured article, i.e., the methods taught herein are not product specific. For instance, the present methods can be applied as easily with respect to diaper components as they can for feminine hygiene products.

Apparatus and methods are provided for folding discrete items such as diapers at high speeds. Discrete items are conveyed in a machine direction toward a pair of vacuum drums rotating in the machine direction and first carrying a top side of a leading edge of the discrete item away from the conveyor, and then carrying a bottom side of the leading edge with a second rotational vacuum drum back towards the conveyor. The diaper fold is created at a contact point with a folding finger which travels rotationally and straight in a fixed orientation about a pair of belts, into and out of contact with the diaper.

BRIEF DESCRIPTION OF THE DRAWINGS

FIGS. 5A and 5B through FIGS. 14A and 14B are side views of the folding system of the present invention operating through an entire folding sequence, and the correlating top views of the operator and drive side blade advancement devices operating through an entire folding sequence.

DESCRIPTION OF THE PREFERRED EMBODIMENT

Although the disclosure hereof is detailed and exact to enable those skilled in the art to practice the invention, the physical embodiments herein disclosed merely exemplify the invention which may be embodied in other specific structures. While the preferred embodiment has been described, the details may be changed without departing from the invention, which is defined by the claims.

It is noted that the present folding techniques and apparatus are described herein with respect to products such as diapers, but as previously mentioned, can be applied to a wide variety of processes in which discrete components are applied sequentially.

Figure 1:
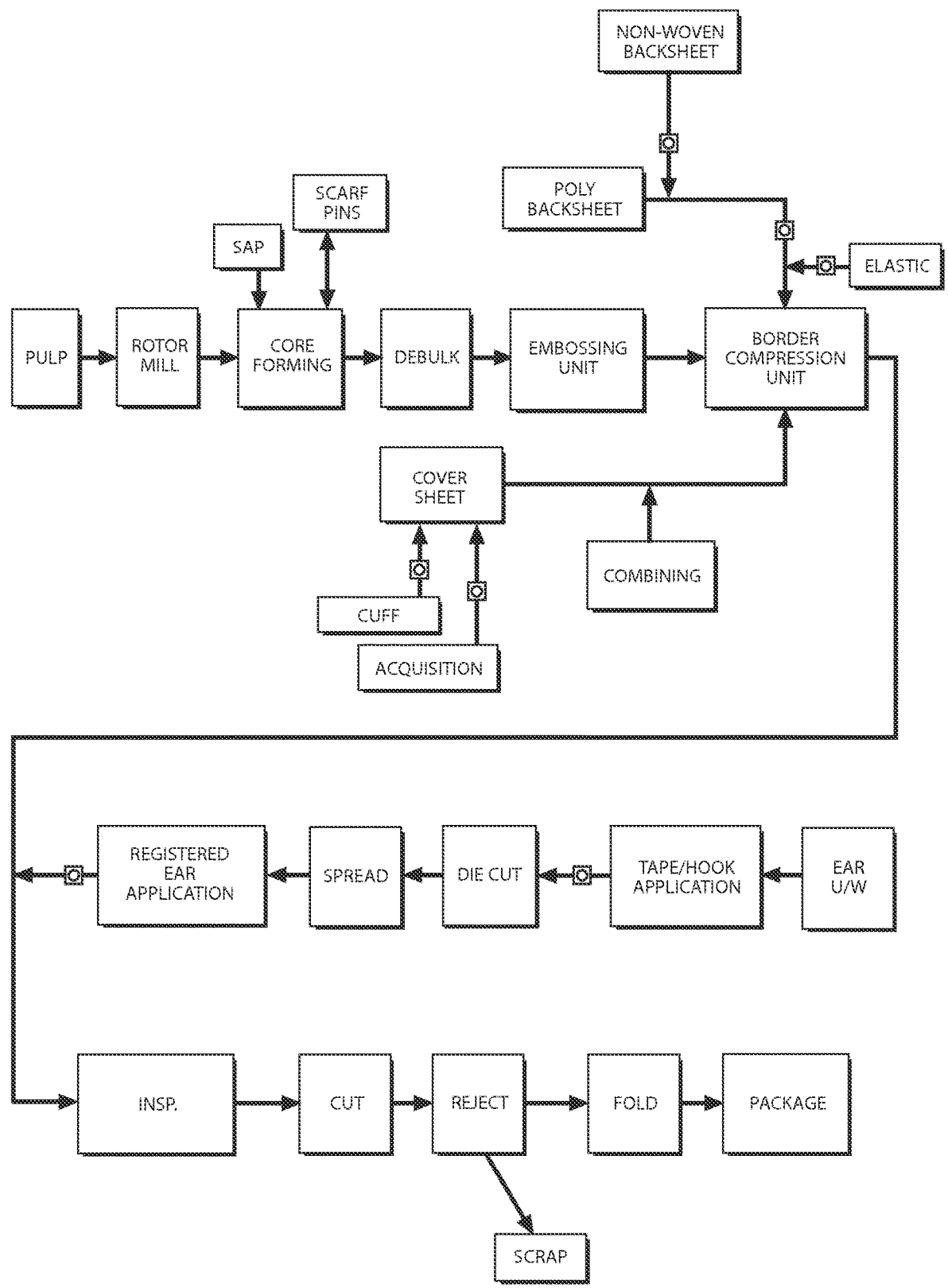
FIG. 1 is a schematic of a representative web processing system.

Referring to FIG. 1, a web processing operation starts with incorporating raw materials such as paper pulp and super absorbent polymer (SAP) in a pulp mill. The mixture is sent to a core forming drum, where cores are formed for retaining liquids. The core undergoes scarfing to trim the core to desired dimensions.

The process continues through debulking, embossing, optionally core cutting and spacing, and optionally, compression. The core can be placed between a preformed cover sheet containing cuff elastics and an acquisition layer, and a backsheet layer, sandwiching the core.

Ears are formed by applying a tape or hook and loop fastening mechanism to an ear web, and ears are die cut and spaced and spread as necessary, for instance as described in U.S. Pat. No. 8,016,972, incorporated herein by reference. The web can undergo folding, extraction and trimming of excess material, and application of material to tighten the diaper about the waist. Eventually, the product is folded and packaged.

As seen on FIG. 1, the ⊡ symbol is shown at locations of introductions of discrete components into the process. At these locations, inspection can take place to determine the presence or absence of acceptable product introduction. In addition to visual inspection, operational characteristics such as startup/ramp-up/shutdown operations can trigger waste minimization techniques as will be described later.

At each of these operations shown in FIG. 1, diagnostics can be performed to indicate whether the product meets acceptable criteria. If so, discrete elements, such as the core, tissue layers, elastic, etc., continue to be applied in a sequence such as shown in FIG. 1. If not, no additional discrete elements need be applied.

The present invention is directed at the folding step in the position indicated on FIG. 1. The device used to perform the folding step is described and shown with reference to the following figures and description.

Figure 2:
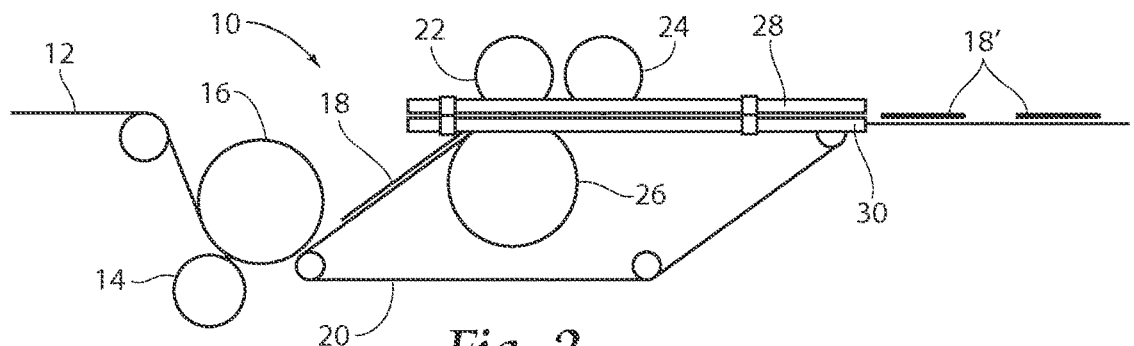
FIG. 2 is a side view of a folding system of the present invention.

Referring now to FIG. 2, a side view of a folding system 10 of the present invention is shown from an operator side of the folding system. An incoming web of material 12 to be folded enters a slip/cut anvil 14 and knife 16 combination to sever the web 12 into discrete pieces 18. The incoming web of material 12 can have ear segments already folded over as described with reference to FIG. 1.

After being severed into a single diaper (or other single discrete component) 18, the diaper is conveyed by a bottom feed conveyor 20 to a combination of vacuum drums 22, 24 and 26 which control movement and initiate the folding as will be described later. A pair of rotating belt units 28 and 30 rotate folding fingers 36 not visible from this view. The folding fingers tuck the diaper to support the folded diaper and the folded diapers 18' are passed downstream to stacking and packaging.

Figure 3A:
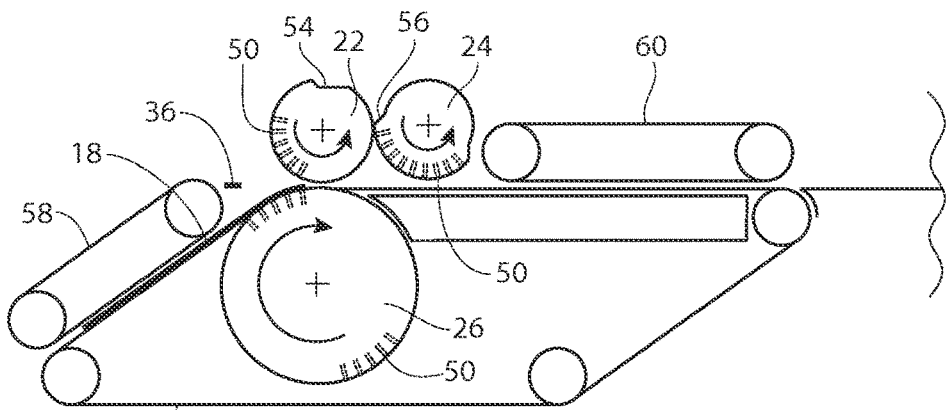
FIG. 3A is a side view of a folding system of the present invention at a beginning point of a folding sequence, with an operator and a drive side folding finger advancement device hidden.
Figure 3B:
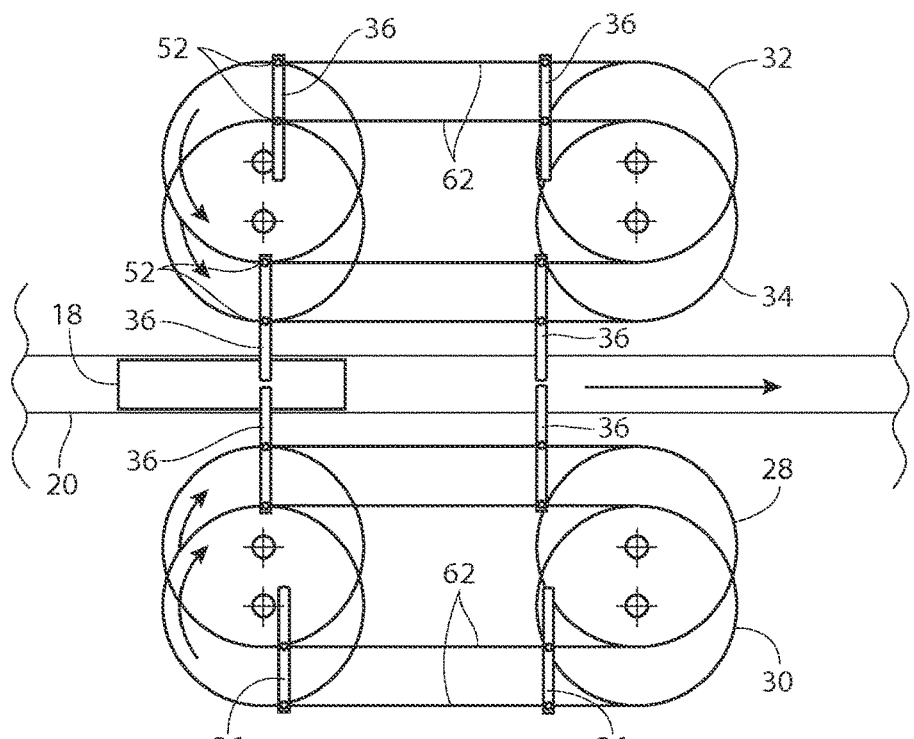
FIG. 3B is a top view of the operator and drive side blade advancement devices of the folding system, shown in sequence with FIG. 4A.

Referring now to FIG. 3A, a side view of the folding system 10 of the present invention at a beginning point of a folding sequence is shown. In this view for simplicity, the operator side rotating belt units 28 and 30, and drive side rotating belt units 32 and 34 are not shown. FIG. 3B is top view of the operator and drive side blade advancement devices of the folding system, shown in sequence with FIG. 3A. FIGS. 3A and 3B, and likewise FIGS. 4A and 4B-FIGS. 14A and 14B are side and top views respectively of the folding system of the present invention operating through an entire folding sequence of a single diaper 18. This sequence is intended to be carried out repeatedly and continuously on a continuous stream of incoming discrete diapers 18.

Referring still to FIG. 3A, a top feed conveyor 58 in conjunction with the bottom feed conveyor 20 transport diaper 18 from the anvil 16/knife 14 combination of FIG. 2. The diaper is carried by a first vacuum drum 26 provided with vacuum ports 50 to transport the diaper 18. A folding finger 36 can be seen approaching the laid out diaper between vacuum rolls 22 and 26, and travels horizontally just above the top horizontal surface of conveyor 20. For simplicity of illustration, a single folding finger 36 is shown in FIG. 3A and subsequent side views, but in a preferred embodiment, two folding fingers 36 will cooperate in tandem to assist in folding of diaper 18. It is noted that a single folding finger 36 could be used in the folding operation, in this embodiment only one tandem of the operator side rotating belt units 28 and 30, or drive side rotating belt units 32 and 34 would be necessary.

Vacuum drum 26 operates clockwise as shown, and vacuum drum 22 operates counterclockwise as shown from an operator side view. The construction and operation of high speed vacuum ported drums 22, 24 and 26 can be constructed according to the vacuum porting design and principles described in U.S. Pat. No. 7,533,709, incorporated herein by reference. In summary of that teaching, the vacuum ported drums 22, 24 and 26 are generally cylindrical bodies connected to a source of vacuum. The drums have a diaper retaining portion on their outer surfaces in order to hold (when desired) and control the path of the diaper 18. The diaper retaining portion is formed with a plurality of vacuum holes on the cylindrical surface. A vacuum slot (not shown) is provided on an end face surface (commutating surface) of the vacuum ported drums 22, 24 and 26 and is adapted to put the plurality of vacuum holes in communication with the vacuum source. In this manner, instantaneous on/off control of vacuum surface ports 50 can be achieved as described in U.S. Pat. No. 7,533,709.

Referring now to FIG. 3B, operator side rotating belt units 28 and 30, and drive side rotating belt units 32 and 34 are shown. Each of operator side rotating belt units 28 and 30, and drive side rotating belt units 32 and 34 the carry a belt 62, and each is rotated for instance by a motor (not shown). In the view shown, in conjunction with FIG. 3A, drive side rotating belt units 32 and 34 rotate counterclockwise and the operator side rotating belt units 28 and 30 rotate clockwise to advance Folding fingers 36 around the travel path of the belt units, with the folding fingers oriented to point upward for the operator side rotating belt units 28 and 30, and downward for drive side rotating belt units 32 and 34. Operator side rotating belt units 28 and 30 cooperate to rotate one or more folding fingers 36 around the travel path of the belt units. Diaper 18 can be seen carried by conveyor 20 in an unfolded condition.

Folding fingers 36 are pivotally mounted by pivotal mounts 52 attaching folding one or more folding fingers 36 to both the operator side rotating belt units 28 and 30, and one or more folding fingers 36 to both drive side rotating belt units 32 and 34. Because a folding finger is pivotally mounted at two points to two simultaneously rotating belts (be they operator side rotating belt units 28 and 30, or drive side rotating belt units 32 and 34), during travel with the belts 62 the orientation of folding fingers 36 remains fixed pointing upward for folding fingers 36 carried by the operator side rotating belt units 28 and 30, and fixed pointing downward for folding fingers 36 carried drive side rotating belt units 32 and 34. The distance between the two belts 62 of the operator side rotating belt units 28 and 30 remains constant, and the distance between the two belts 62 of drive side rotating belt units 32 and 34 also remains constant. The operator side rotating belt units 28 and 30 are spaced apart from one another in a cross machine direction at a distance equal to the intended distance for cross-machine direction travel of folding fingers 36 during the folding sequence. The drive side rotating belt units 32 and 34 also are spaced apart from one another in a cross machine direction at a distance equal to the intended distance for cross-machine direction travel of folding fingers 36 during the folding sequence.

Although four folding fingers 36 are shown carried by belts 62 of operator side rotating belt units 28 and 30 and drive side rotating belt units 32 and 34, more or less can be used according to preference. As noted, a single folding finger 36 could be used in the folding operation to fold a single diaper 18, but in a preferred embodiment as shown in FIG. 3B, two folding fingers 36 each act on a single diaper 18, each folding finger 36 extending nearly roughly to a centerline of the diaper 18 in the cross-machine direction.

Figure 4A:
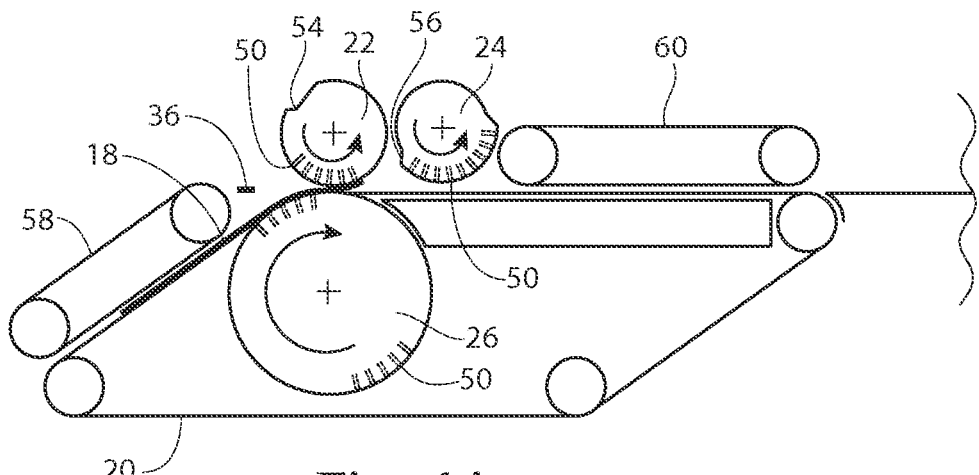
FIGS. 4A and 4B, and likewise
Figure 4B:
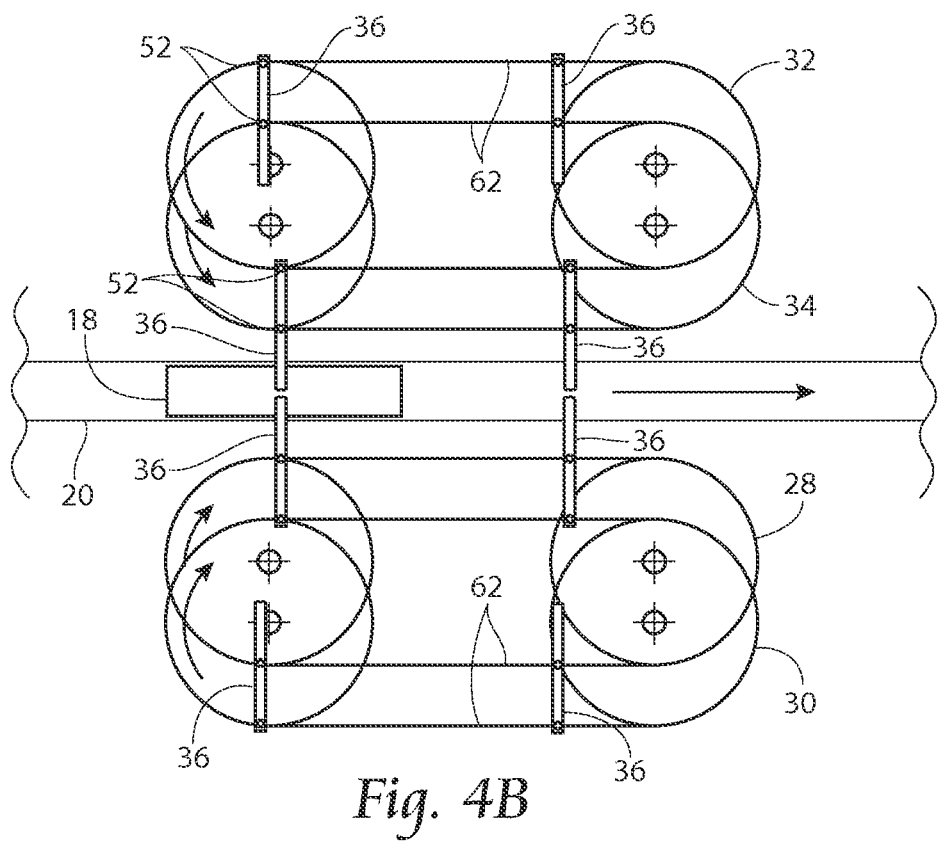

Referring to FIGS. 4A and 4B together as the folding sequence advances, a leading edge of discrete diaper 18 has been picked up by rotating vacuum drum 22 by vacuum ports 50 which are activated as previously described.

Figure 5A:
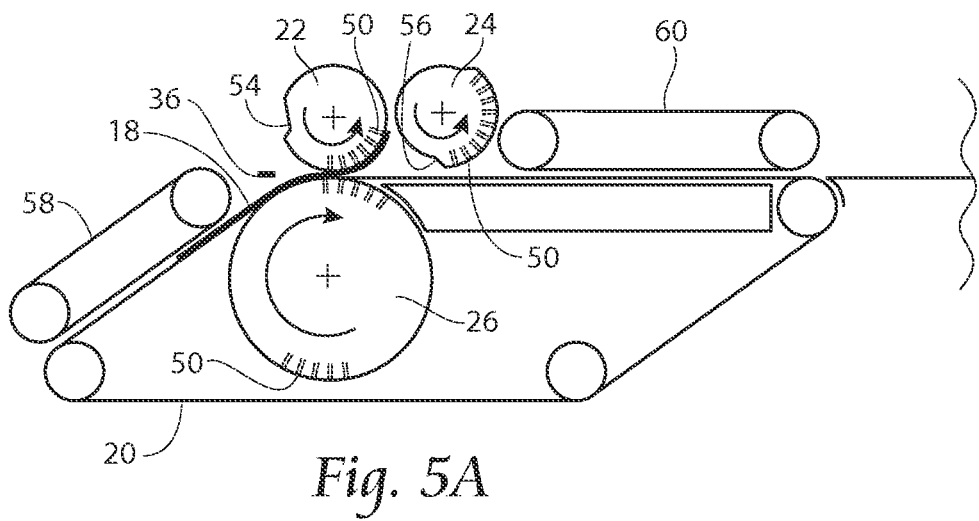
Figure 5B:
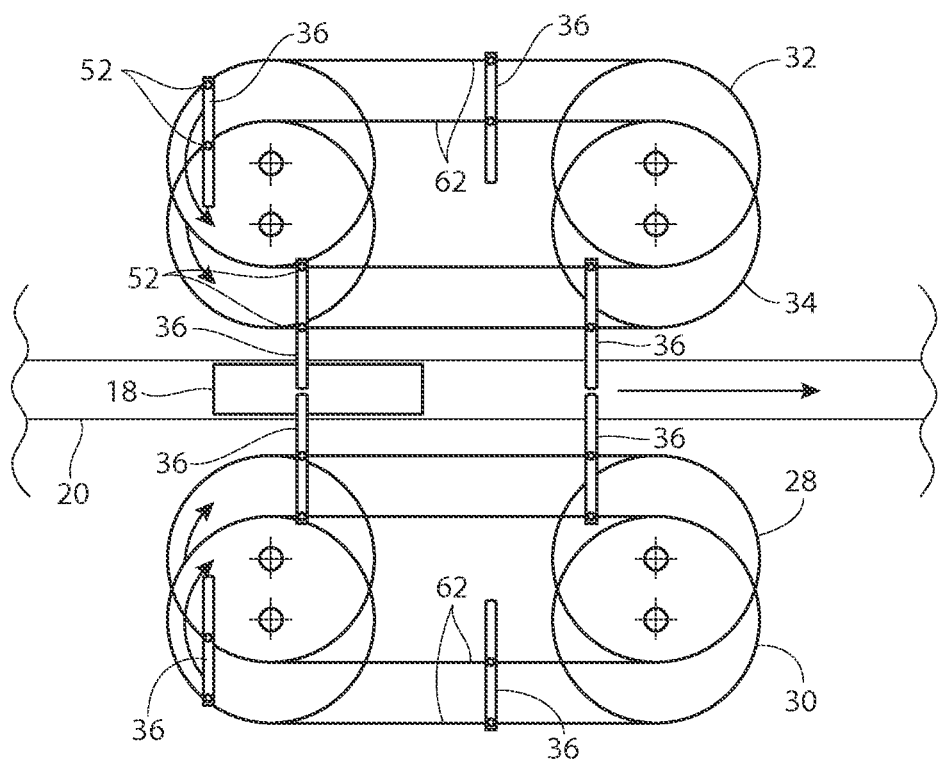

As shown in FIGS. 5A and 5B, rotating vacuum drum 22 has carried the leading edge of diaper 18 further away from rotating drum 26 and conveyor 20, and folding finger 36 approaches a midsection of diaper 18. The folding fingers 36 carried by belts 62 of operator side rotating belt units 28 and 30 and drive side rotating belt units 32 and 34 have advanced accordingly, at preferably about the same speed as the conveyor 20 carrying diaper 18.

Figure 6A:
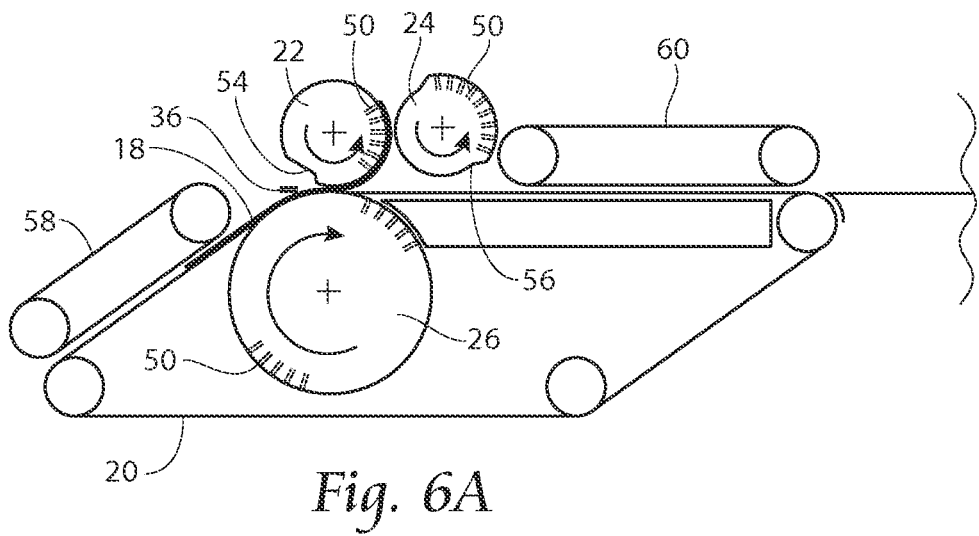
Figure 6B:
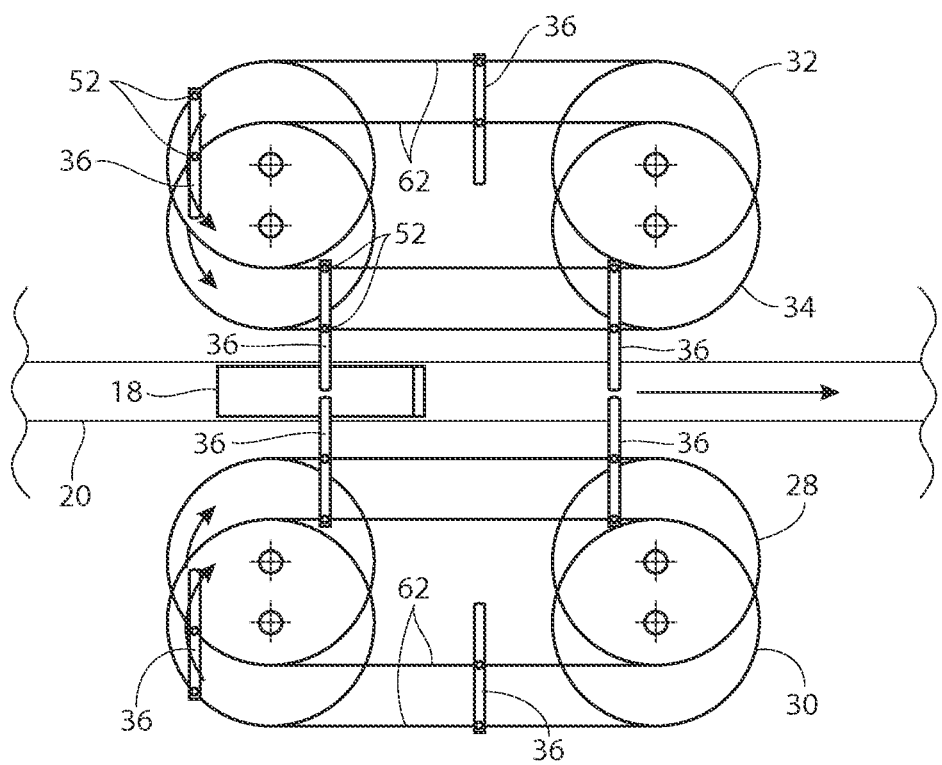

Referring to FIGS. 6A and 6B, folding finger 36 approaches closer to the midsection of diaper 18, and is seen traveling above vacuum drum 26 and about to enter a notched portion 54 of the otherwise cylindrical vacuum drum 22. The notched portion 54 is provided to allow passage of the folding finger 36 past the vacuum drum 22. The folding fingers 36 carried by belts 62 of operator side rotating belt units 28 and 30 and drive side rotating belt units 32 and 34 have advanced accordingly, as shown on FIG. 6B.

Figure 7A:
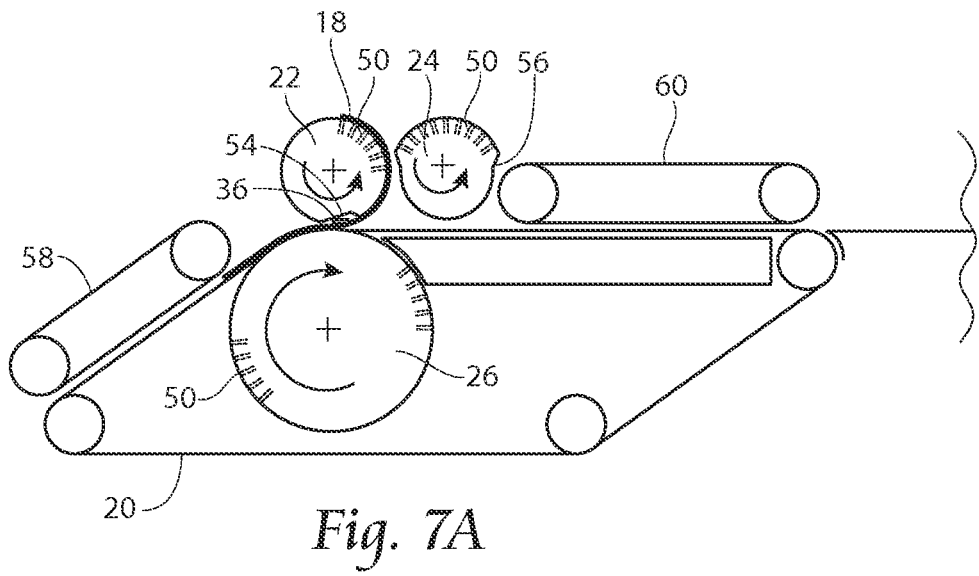
Figure 7B:
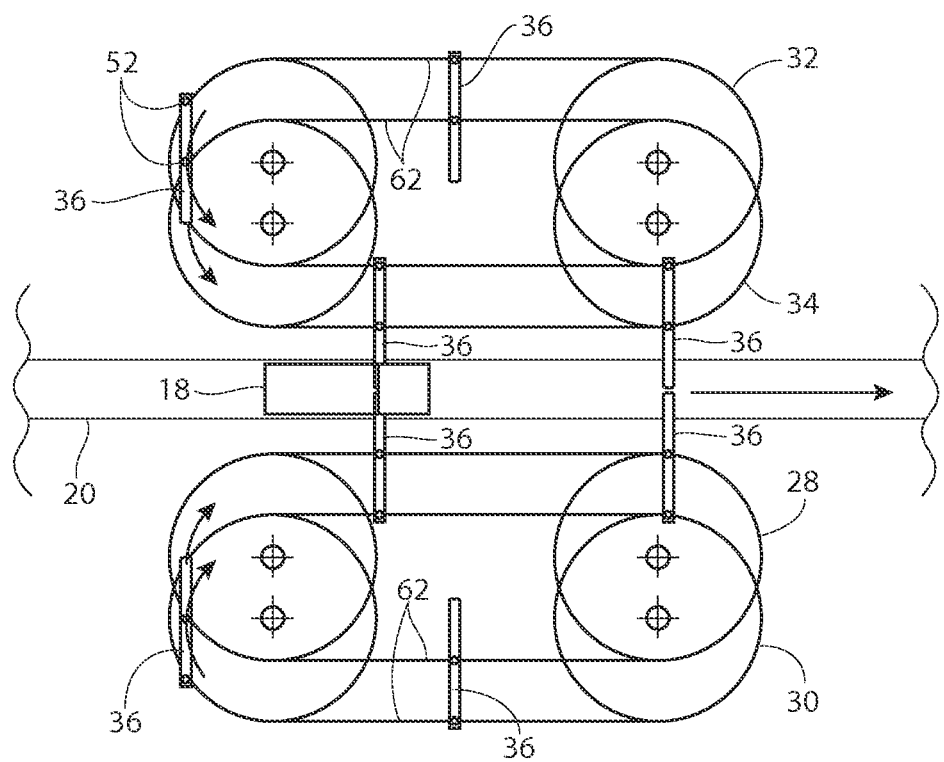

Referring to FIGS. 7A and 7B, folding finger 36 has entered notched portion 54 of the otherwise cylindrical vacuum drum 22 and contacted a midsection of diaper 18 to initiate a fold at the point of contact, while the leading edge of diaper 18 is still carried by rotating vacuum drum 22. The folding fingers 36 carried by belts 62 of operator side rotating belt units 28 and 30 and drive side rotating belt units 32 and 34 have advanced accordingly, as shown on FIG. 7B.

Figure 8A:
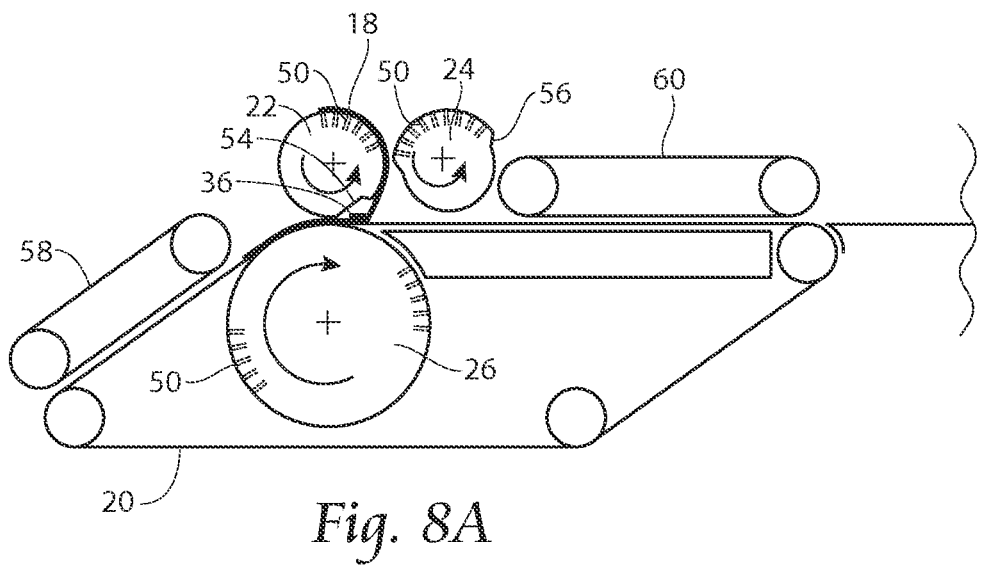
Figure 8B:
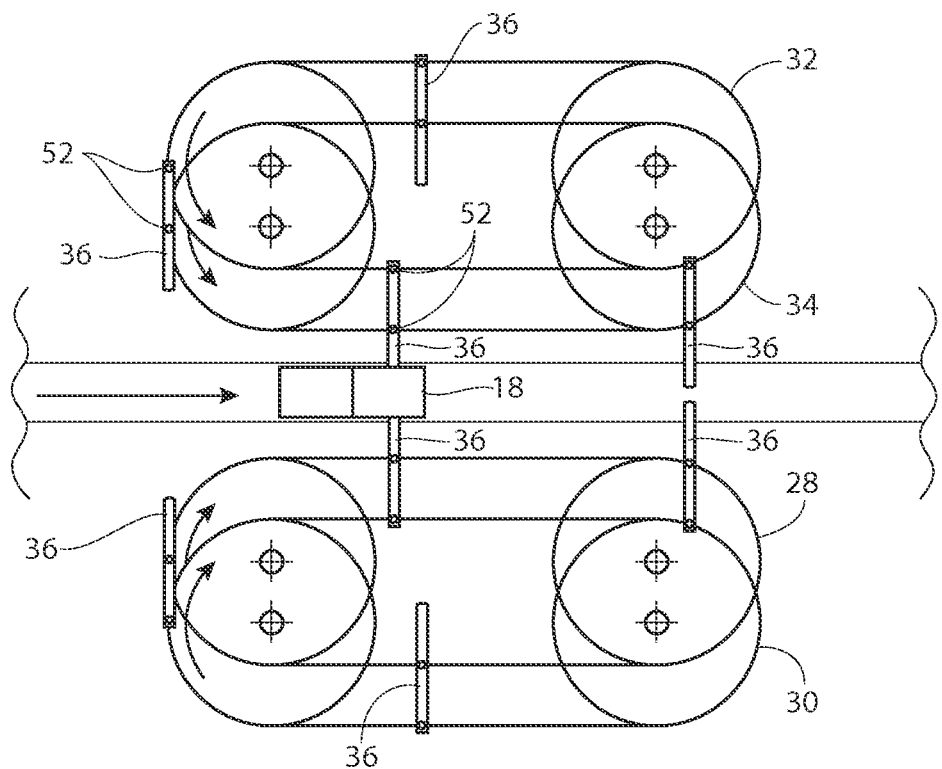

Referring to FIGS. 8A and 8B, folding finger 36 continues its horizontal path just above the top horizontal surface of conveyor 20 and maintains the midsection of diaper 18 on conveyor 20. The folding fingers 36 carried by belts 62 of operator side rotating belt units 28 and 30 and drive side rotating belt units 32 and 34 have advanced accordingly, as shown on FIG. 8B.

Figure 9A:
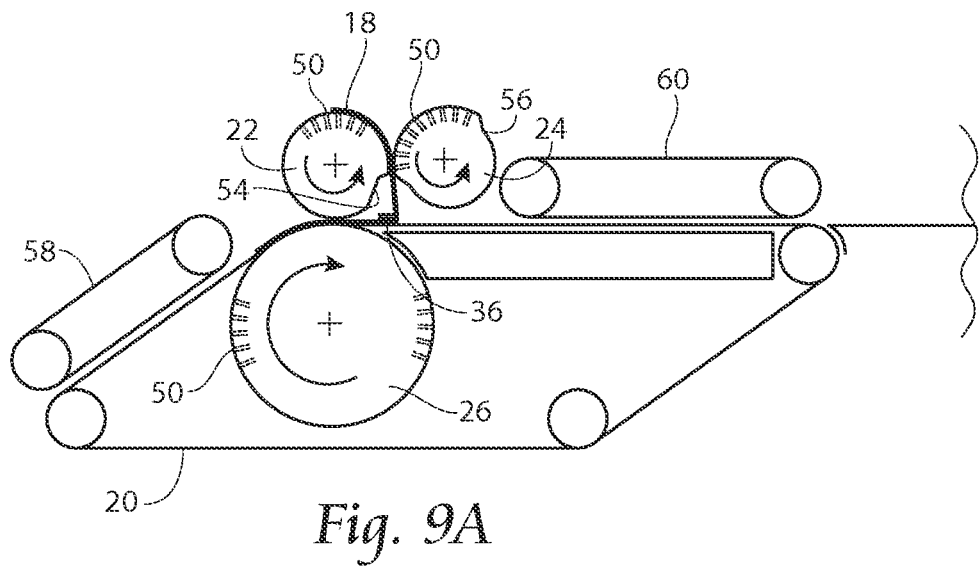
Figure 9B:
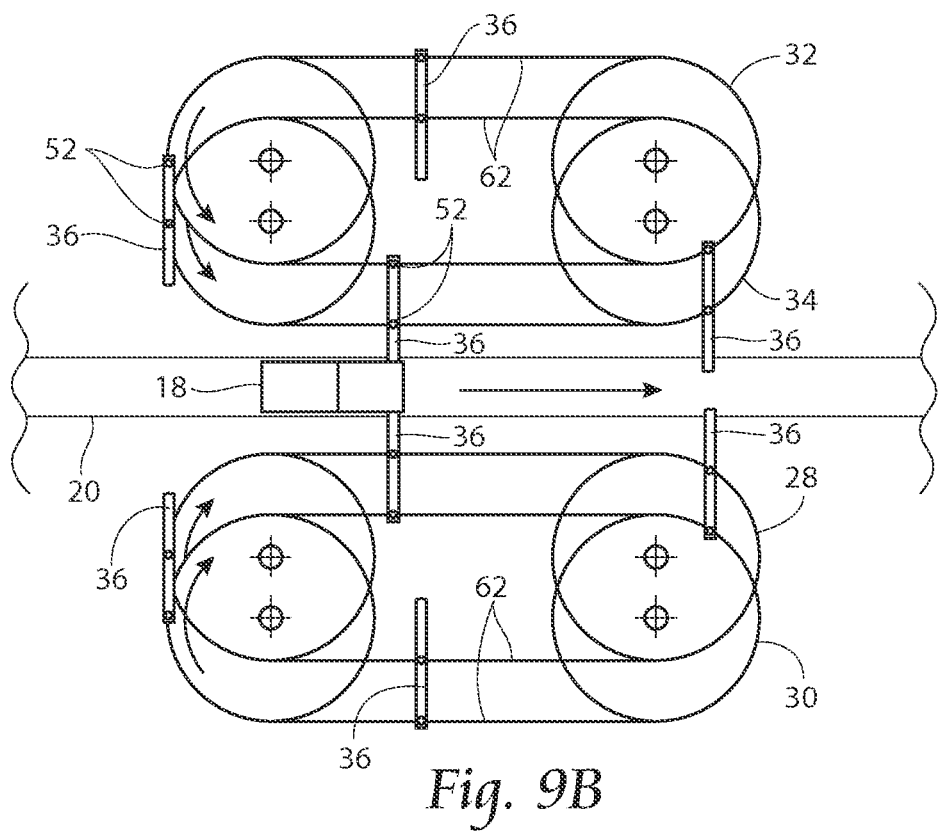

Referring to FIGS. 9A and 9B, vacuum ports 50 on drum 22 have been deactivated past a maximal counterclockwise downstream advance of leading edge of diaper 18, and vacuum ports 50 on drum 24 rotating counterclockwise have been activated. Drum 24 engages what was previously an underside of diaper 18 but has now become a topside of diaper 18. Drums 22 and 24 are closely spaced together at this point in the folding process to maintain control of diaper 18. At points previous to this in the folding process, extended notch 56 creates a non-contacting surface area of drum 24 that has prevented drum 24 from contacting the diaper 18, along drum 22 to carry diaper 18 counterclockwise without interference. The folding fingers 36 carried by belts 62 of operator side rotating belt units 28 and 30 and drive side rotating belt units 32 and 34 have advanced accordingly, as shown on FIG. 9B.

Figure 10A:
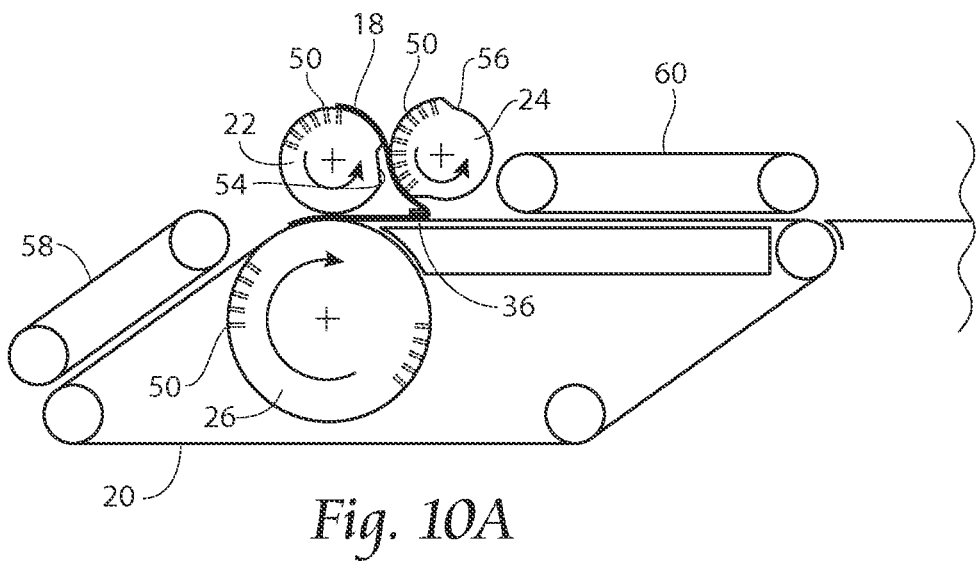
Figure 10B:
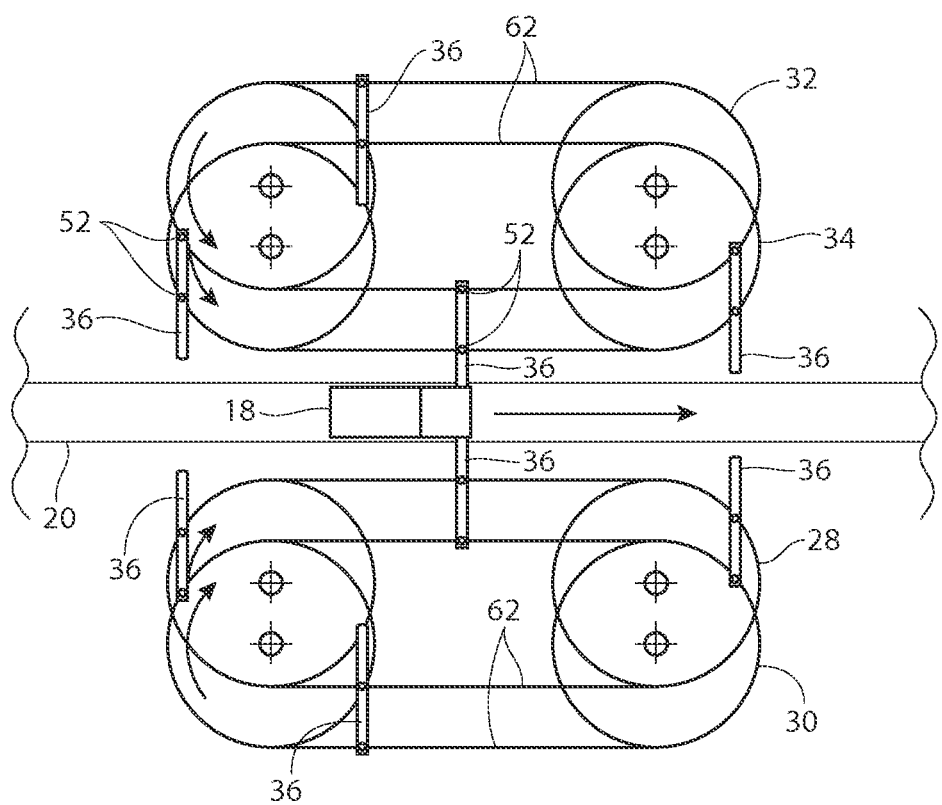
Figure 11A:
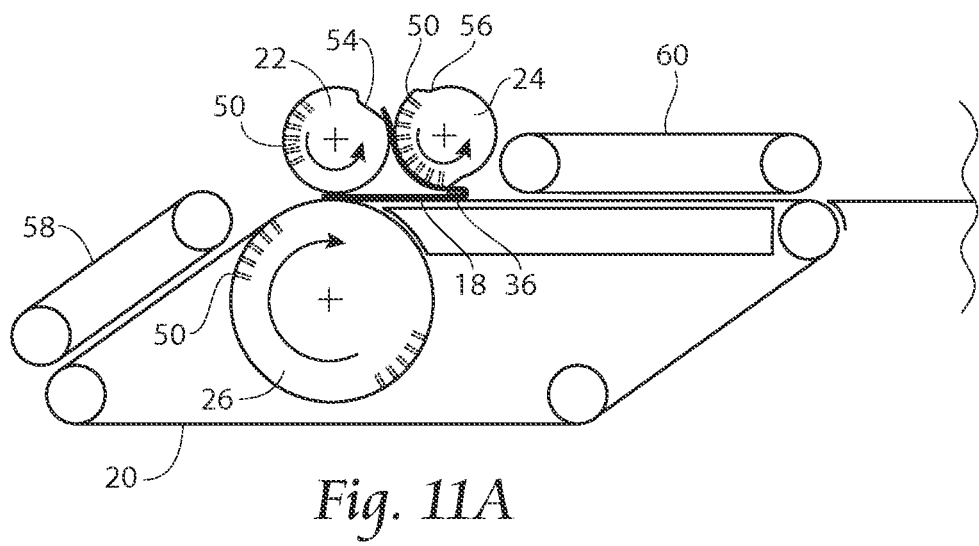
Figure 11B:
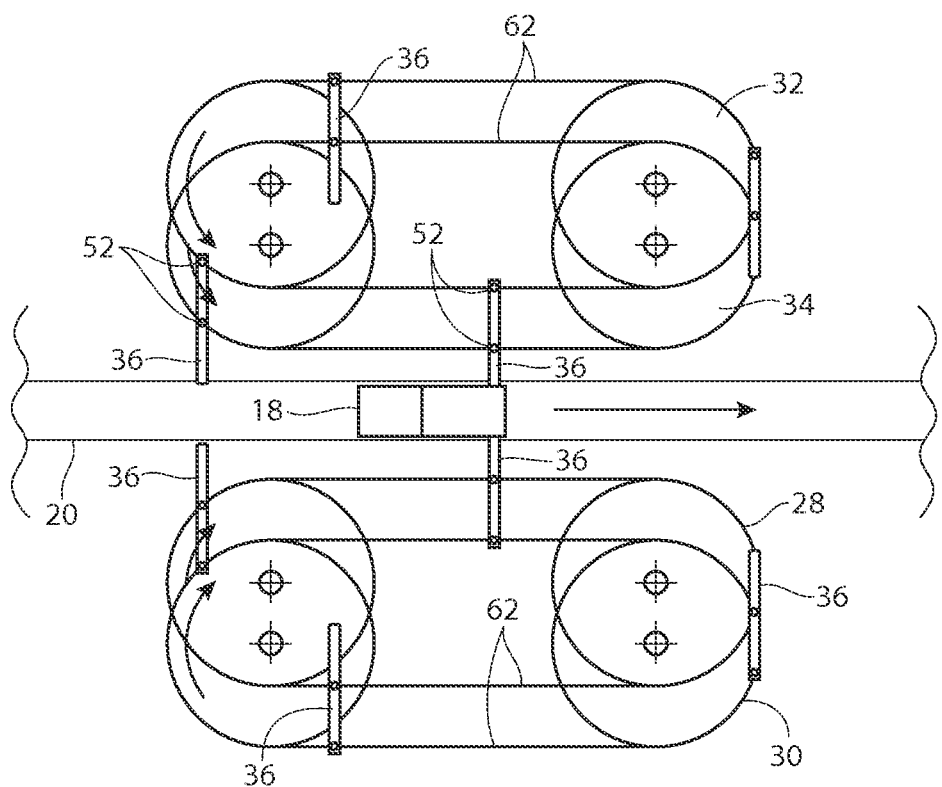
Figure 12A:
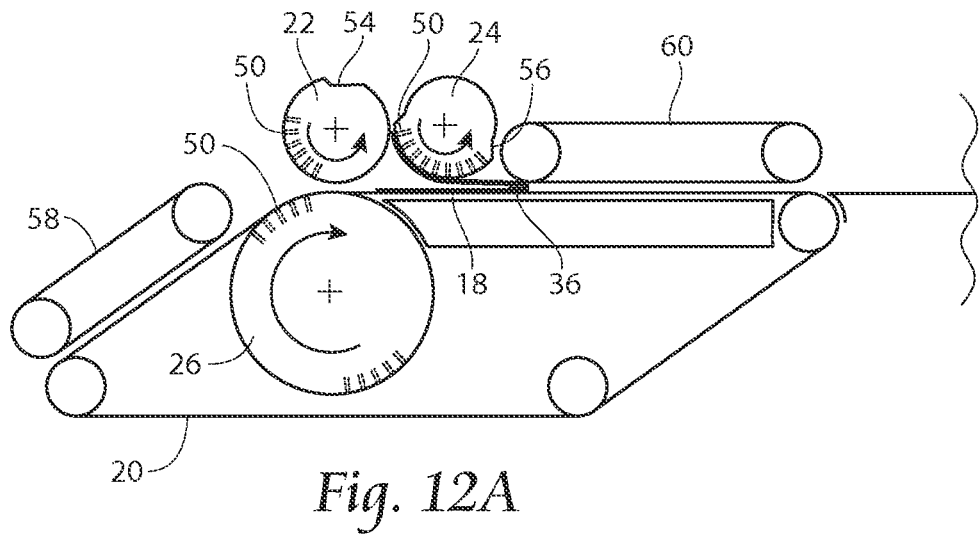
Figure 12B:
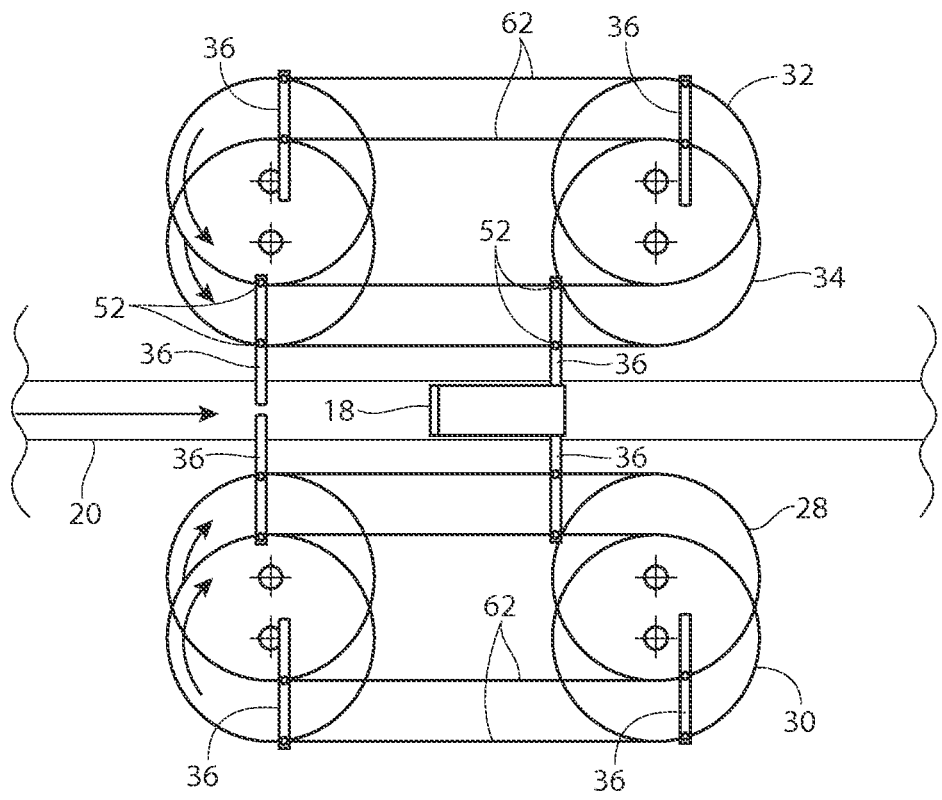

Referring to FIGS. 10A and 10B, drum 24 rotating counterclockwise assists the leading portion of diaper 18 downwards during rotation back towards conveyor 20 to lay the leading half of the diaper over the trailing half of the diaper. The counterclockwise rotational velocity of the outermost perimeter of drum 24 is substantially equal to the speed of conveyor 20, as well as substantially equal to the counterclockwise rotational velocity of the outermost perimeter of drum 22 to avoid shear forces on diaper 18 and to establish a controlled laydown of the leading half of folded diaper 18. The folding fingers 36 carried by belts 62 of operator side rotating belt units 28 and 30 and drive side rotating belt units 32 and 34 have advanced accordingly, as shown on FIG. 10B.

Figure 13A:
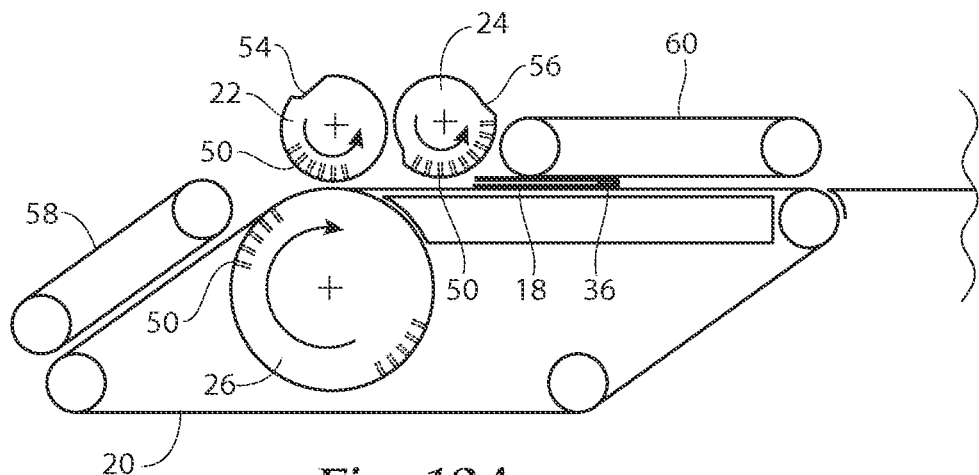
Figure 13B:
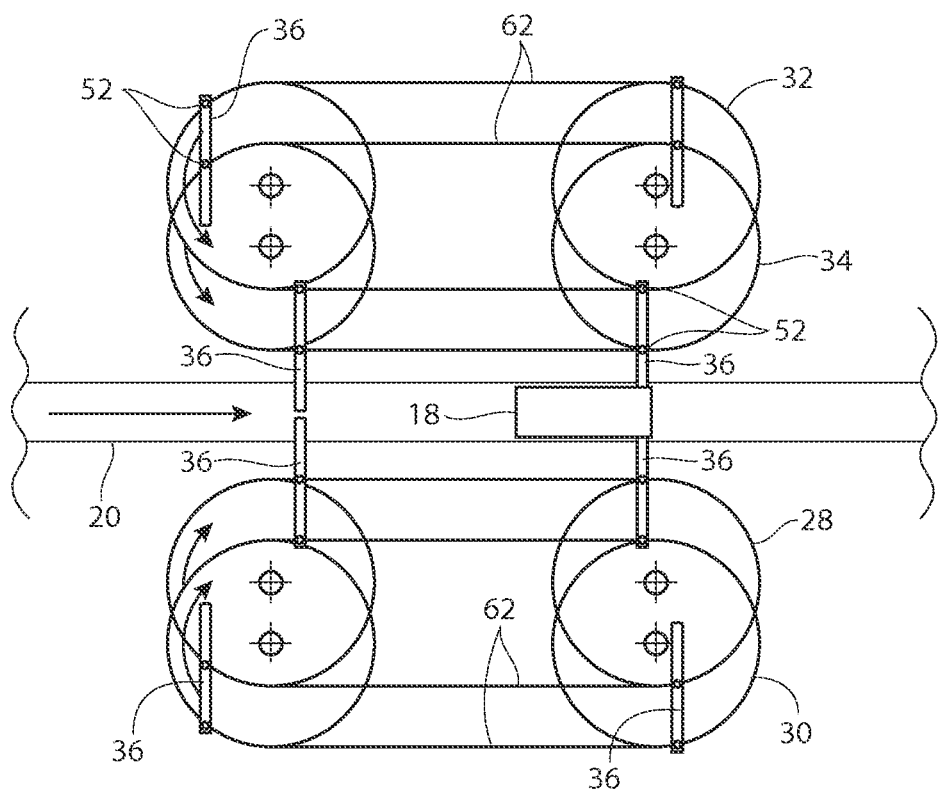

The folding process continues in sequence through FIGS. 11A and 11B, and 12A and 12B, until the fold is completed and the folded diaper 18 is completely folded and the top of diaper 18 is released from vacuum ports 50 of drum 24 as shown in FIG. 13A.

Figure 14A:
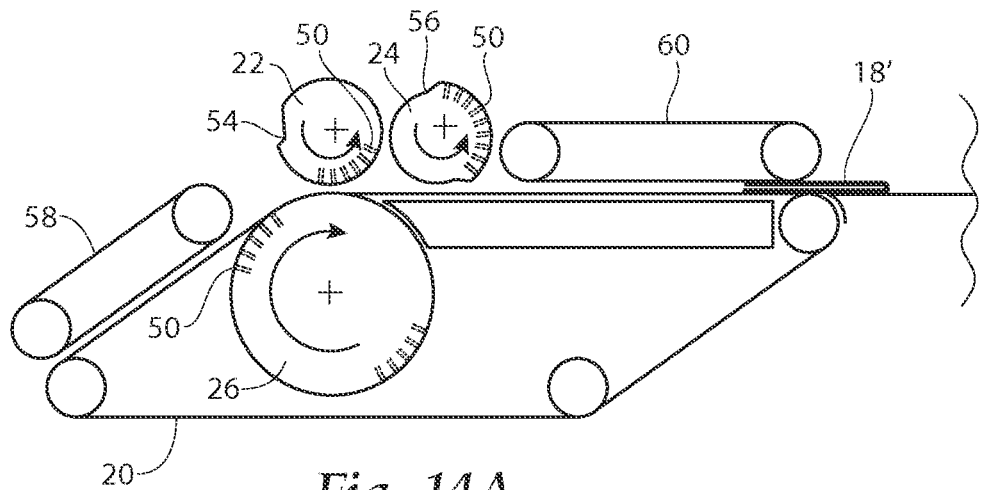
Figure 14B:
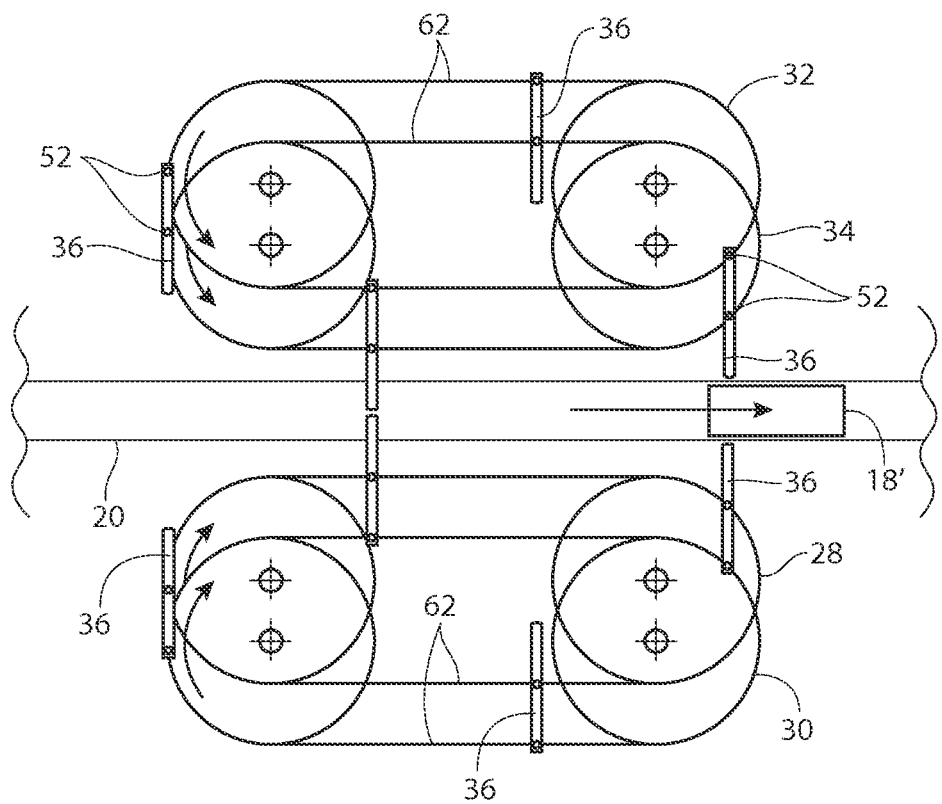

Referring now to FIGS. 14A and 14B, folding fingers 36 round downstream corners of operator side rotating belt units 28 and 30, and drive side rotating belt units 32 and 34 and are thereby withdrawn from the folded diaper 18 in the cross-machine direction, and free to travel along their counterclockwise path until rounding upstream corners of operator side rotating belt units 28 and 30, and drive side rotating belt units 32 and 34 to return to the beginning of the folding process and start anew. Downstream conveyor 60, along with conveyor 20, carry the folded diaper 18' downstream for further processing as desired, such as stacking and packaging.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

The invention claimed is:

1. A method for folding discrete items comprising:
conveying an item in a machine direction with a first conveyor, carrying said item on a first side;
carrying a second side of a leading portion of said item and rotating said leading portion in a first rotational direction with a first drum continuously rotating in said first rotational direction;
contacting a midsection of said item in a folding plane with a folding finger traveling in said machine direction, said folding finger traveling about a travel path in said folding plane;
releasing said second side of said leading portion of said item from said first drum while rotating said first drum in said first rotational direction;
carrying said first side of said leading portion of said item and rotating said leading portion in said first rotational direction with a second drum that continuously rotates in said first rotational direction;
releasing said first side of said leading portion of said item to lay said leading portion of said item atop a trailing portion of said item;
wherein said folding finger is maintained in a constant cross-machine direction orientation and in said folding plane as said folding finger travels about an entirety of said travel path.

2. The method according to claim 1, the method further comprising contacting said midsection of said item with a second folding finger traveling in said machine direction.

3. The method according to claim 2, wherein said first and said second folding fingers contact approximately just less than one half of said item in a cross-machine direction.

4. The method according to claim 1, wherein said folding finger travels in said folding plane at all times, both during contacting said midsection of said item while performing folding thereof and during travel of said folding finger in a direction opposite said machine direction when returning said folding finger to a position upstream of said first drum.

5. The method according to claim 1 wherein said folding finger travels at a same speed as said first conveyor.

6. A machine for folding discrete items comprising:
a first conveying unit for carrying said discrete items on a first side at a first velocity in a machine direction;
a first rotating drum rotating in a machine direction, said first rotating drum carrying said discrete items on a second side at a leading portion, said first rotating drum providing a holding force to said second side of said discrete items;

a folding finger disposed in a folding plane over which said discrete items are folded, said folding finger disposed in a constant cross-machine direction orientation and traveling in said folding plane so as to be maintained in said folding plane, said folding finger contacting a midsection of said discrete items on said second side; and a second rotating drum rotating in said machine direction and carrying said leading portion of said discrete items on said first side at said first velocity, and laying down said leading portion of said discrete items atop a trailing edge of said discrete items, said second rotating drum providing a holding force to said first side of said discrete items;

wherein said folding finger travels about a travel path such that said folding finger passes between said first rotating drum and said first conveying unit as said first rotating drum carries said second side, and such that said folding finger passes between said second rotating drum and said first conveying unit as said second rotating drum carries said first side;

wherein said folding finger is maintained in said constant cross-machine direction orientation and in said folding plane as said folding finger travels about an entirety of said travel path.

7. The machine according to claim 6, the machine further comprising a pair of operator side rotating belt units each carrying a belt, said folding finger coupled to both of said belts.

8. The machine according to claim 7, wherein said folding finger is coupled to at least one of said belts by a pivotal coupling, said folding finger disposed and maintained in the constant cross-machine direction during rotation of said belts.

9. The machine according to claim 7, wherein said operator side rotating belt units are spaced apart in a cross-machine direction.

10. The machine according to claim 6, the machine further comprising a pair of drive side rotating belt units each carrying a belt, said folding finger coupled to both of said belts.

11. The machine according to claim 10, wherein said folding finger is coupled to at least one of said belts by a pivotal coupling, said folding finger disposed and maintained in the constant cross-machine direction during rotation of said belts.

12. The machine according to claim 10, wherein said drive side rotating belt units are spaced apart in a cross-machine direction.

13. The machine according to claim 6, wherein at least one of said first and second rotating drums comprises a vacuum drum for providing a holding force to said discrete items, said at least one of said first and second rotating drums coupled to a source of vacuum.

14. The machine according to claim 6, wherein said folding finger remains in said folding plane during an entirety of its travel about said travel path, both as said folding finger travels in the machine direction and as said folding finger travels in a direction opposite said machine direction when returning said folding finger to a position upstream of said first rotating drum.

15. The machine according to claim 6, wherein each of said first rotating drum and said second rotating drum rotate only in said machine direction.

16. A machine for folding discrete items comprising:

a first conveying unit for carrying said discrete items at a first velocity on a first side in a machine direction during a folding operation;

a first rotating drum rotating in a machine direction, said first rotating drum carrying said discrete items on a second side at a leading portion, said first rotating drum providing a holding force to said discrete items;

a folding finger contacting a midsection of said discrete items on said second side, said folding finger carried at a first point of said folding finger by a first rotating unit, said first rotating unit spaced at a first cross-machine direction distance from said first conveying unit;

said folding finger carried at a second point of said folding finger by a second rotating unit, said second rotating unit spaced at a second cross-machine direction distance from said first conveying unit, said second cross-machine direction distance greater than said first cross-machine direction distance;

said first and second rotating units operating to retain said folding finger in substantially the same plane throughout rotation thereof, about an entirety of a travel path about which said folding finger travels;

said first and second points of said folding finger spaced apart at a constant cross-machine direction distance from each other, and said first and second points of said folding finger spaced apart at a variable cross-machine direction distance from said first conveying unit;

a second rotating drum rotating in the machine direction and carrying said leading portion of said discrete items on said first side at said first velocity, and laying down said leading portion of said discrete items atop a trailing edge of said discrete items, said second rotating drum providing a holding force to said discrete items;

wherein said folding finger is maintained in a constant cross-machine direction orientation throughout rotation thereof about said travel path by said first and second rotating units.

17. The machine according to claim 16, wherein each of said first rotating drum and said second rotating drum rotate continuously in said machine direction.

\* \* \* \* \*